US00PP31010P2

(12) United States Plant Patent
Bloodworth

(10) Patent No.: US PP31,010 P2
(45) Date of Patent: Nov. 5, 2019

(54) GRAPEVINE PLANT NAMED 'JB06-43-6-22'

(50) Latin Name: **Intersubgeneric hybrid of *Vitis Muscadinia* Planch. and *Vitis Euvitis* Planch.**
Varietal Denomination: JB06-43-6-22

(71) Applicant: Patterson Jeffrey Bloodworth, Hillsborough, NC (US)

(72) Inventor: Patterson Jeffrey Bloodworth, Hillsborough, NC (US)

( * ) Notice: Subject to any disclaimer, the term of this patent is extended or adjusted under 35 U.S.C. 154(b) by 0 days.

(21) Appl. No.: 16/350,999

(22) Filed: Feb. 11, 2019

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./156, 205
See application file for complete search history.

(56) References Cited

U.S. PATENT DOCUMENTS 9,706,726 B2 * 7/2017 Bloodworth ..... A01H 5/08

* cited by examiner

*Primary Examiner* — Susan McCormick Ewoldt
*Assistant Examiner* — Karen M Redden
(74) *Attorney, Agent, or Firm* — Barbara Campbell; Cochran Freund & Young LLC

(57) ABSTRACT

A new grapevine plant particularly distinguished by medium-sized seedless fruit, typical, pronounced aroma and flavor of *V. rotundifolia*, with very juicy flesh, and a healthy, vigorous vine, having the phenotype of a muscadine, is disclosed.

2 Drawing Sheets

Genus and species: Intersubgeneric hybrid of *Vitis Muscadinia* Planch. and *Vitis Euvitis* Planch.
Variety denomination: 'JB06-43-6-22'.

BACKGROUND OF THE NEW PLANT

The present invention relates to a new and distinct variety of grapevine and hereinafter referred to by the variety name 'JB 06-43-6-22'. Variety 'JB 06-43-6-22' is a new variety of seedless grape.

'JB06-43-6-22' arose from a controlled pollination in June 2006 in Hillsborough, N.C. between the *Vitis Muscadinia* Planch. female parent 'JB99-1-4-15' (unpatented) and the male parent 'JB03-20-1-21' (unpatented), a hybrid of *Vitis Muscadinia*, (primarily *V. rotundifolia* with admixture of *V. munsoniana*) and *Vitis Euvitis* (primarily *V. vinifera* with admixture of various other *Euvitis* species). The seeds from this controlled pollination were planted in February 2017.

'JB06-43-6-22' was selected in October 2008 in Hillsborough, N.C. from among a population of seedlings resulting from the closed pollination of the parental lines.

'JB06-43-6-22' was first asexually propagated in July 2014 in Hillsborough, N.C. via softwood cuttings propagated under intermittent mist. Further observations demonstrated that the characteristics of this new variety are stable, and 'JB06-43-6-22' was found to reproduce true to type in successive generations of asexual propagation via softwood cuttings.

SUMMARY

The following are the most outstanding and distinguishing characteristics of this new variety when grown under normal horticultural practices in Hillsborough, N.C.

1. Medium-sized seedless stenospermocarpic fruit;
2. Typical, pronounced aroma and flavor of *V. rotundifolia*, with very juicy flesh; and
3. A healthy, vigorous vine, having the phenotype of a muscadine.

DESCRIPTION OF THE PHOTOGRAPHS

This new grapevine plant is illustrated by the accompanying photographs which shows the plant's overall plant habit including form, fruit, and foliage. The photographs are of a 10-year old plant taken in October 2017 and grown outdoors in Hillsborough, N.C. The colors shown are as true as can be reasonably obtained by conventional photographic procedures.

Figure 1:
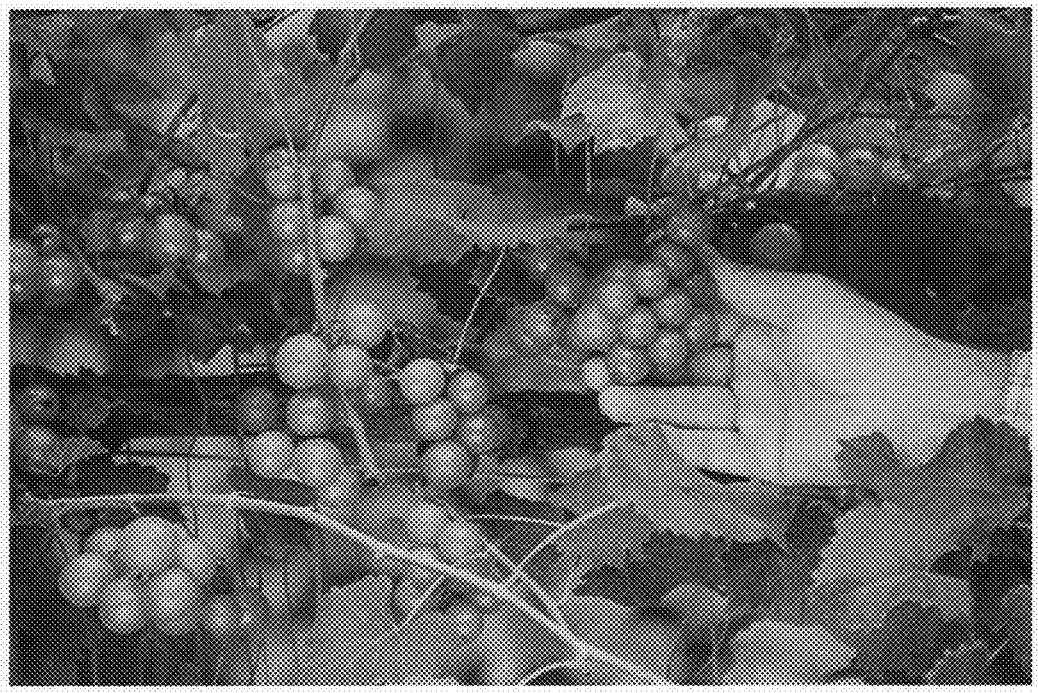
Figure 2:
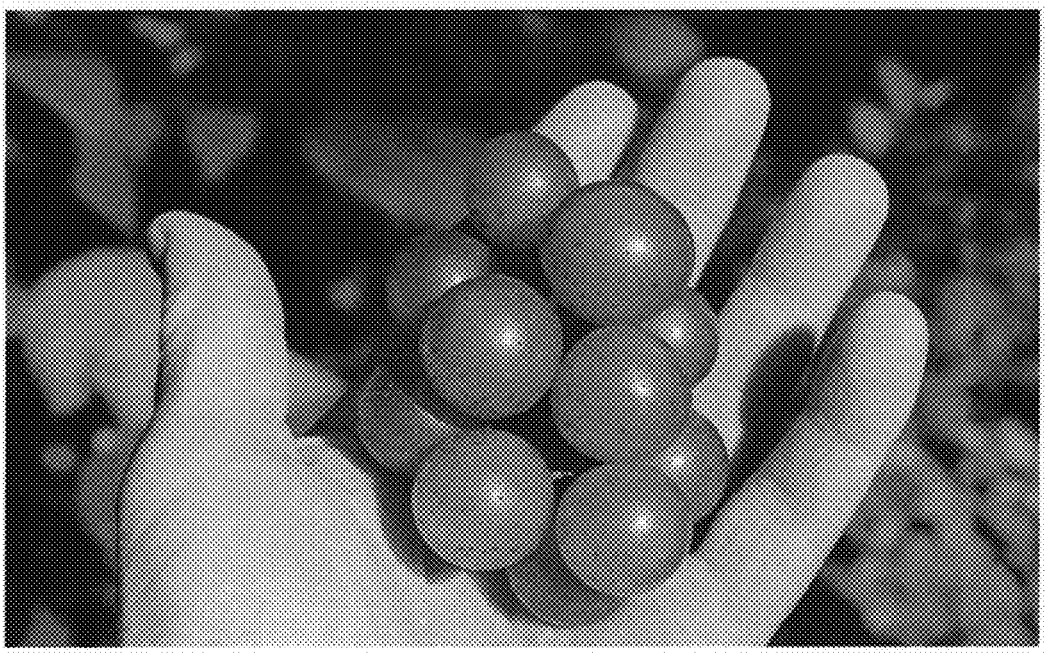
Figure 3:
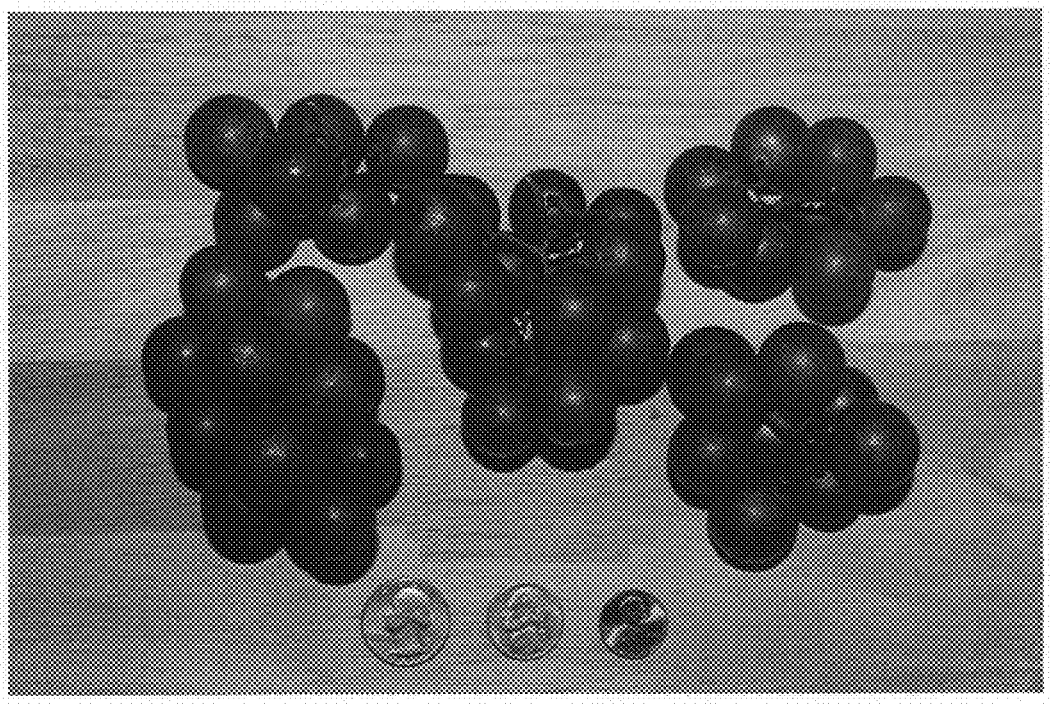
Figure 4:
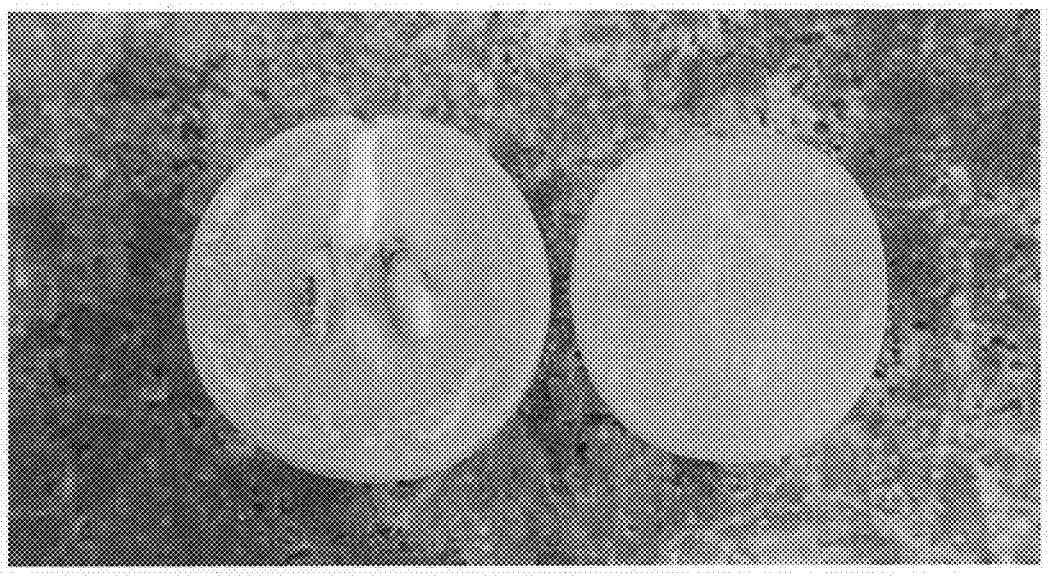

FIG. 1 shows the overall vines, foliage, and fruit clusters.
FIG. 2 shows a close-up of an individual cluster of fruit.
FIG. 3 shows several individual fruit clusters.
FIG. 4 shows berry cross-sections of a commercial seeded variety, 'Fry'(U.S. Plant Pat. No. 7,296), on the left and of seedless 'JB06-43-6-22' on the right.

DESCRIPTION OF THE NEW VARIETY

The following detailed descriptions set for the distinctive characteristics of 'JB06-43-6-22'. The data which define these characteristics were collected from the original seedling vine carried out in Hillsborough, N.C. in October 2018 on the 11-year-old plant. Observations were taken indoors under a dissecting microscope with white fiber optic lighting and outdoors under natural light. Color references are to the colour chart of The Royal Horticultural Society of London (R.H.S.) 2007, Fifth Edition.

Classification:

*Family*.—Vitaceae.

*Botanical*.—Intersubgeneric hybrid of *Vitis Muscadinia* Planch. and *Vitis Euvitis* Planch.

*Primary species*.—*V. rotundifolia* Michx. and *Vitis vinifera* L.

*Designation*.—'JB06-43-6-22'.

Plant:

*Plant habit and growth*.—Recumbent, climbing.

*Size*.—Large.

*Height*.—6 feet at maturity.

*Width*.—4 feet at maturity.

*Age at maturity*.—3 years.

*Vigor*.—High.

*Productivity*.—Medium-high; production potential is 2.5 tons per acre on vines spaced 20 feet in row and 10 feet between rows on a single wire trellis with vines pruned to 200 nodes per vine; the storability of the fruit is undetermined to date.

*Cold hardiness/winter hardiness/temperature tolerance*.—The original vine of 'JB06-43-6-22', after exposure to minus 2 degrees Fahrenheit in January 2018, lost 4 feet out of 11 feet of cordon to cold injury, however the trunk was not injured and the vine vigor and production remains normal on the remaining cordon. 'JB06-43-6-22' may be less cold hardy than the standard muscadine cultivars, 'Carlos' (unpatented) and 'Noble' (unpatented), but more-cold hardy than 'RazzMatazz' (unpatented). In prior exposures of temperatures down to zero degrees Fahrenheit, 'JB06-43-6-22' has not shown any other than a slight degree of cold injury, such as the loss of a minimal number of one-year buds.

Trunk:

*Diameter*.—2⅛ inches.

*Surface texture*.—Smooth on newly exposed bark, otherwise, rough.

*Color*.—New bark is RHS 173D and old bark is RHS N200B.

Canes:

*Diameter*.—¼ inch-7/32 inch.

*Length*.—Variable, ranging from 6 feet to 12 feet.

*Surface texture, immature cane*.—Smooth, lenticels not as raised as in mature canes.

*Surface texture, mature cane*.—Rough with numerous raised lenticels.

*Form* (*woody cross-section form*).—Elliptical.

*Color, immature*.—RHS 146C at 4 weeks.

*Color, mature*.—RHS 165B at 6 months.

*Internode length* (*upper mature sun cane*).—Variable, ranging from 2¼ inches to 4½ inches.

Time of bud burst: April 7 to 17.

Tendrils:

*Form*.—Unbranched.

*Size*.—Large.

*Length*.—Up to 6 inches.

*Diameter*.—1/32 inch.

*Texture and distribution*.—Smooth, at node opposite petiole, absent at every third node.

*Color, immature*.—RHS 144A, near the shoot tip; anthocyanin is absent.

*Color, mature*.—RHS 173A, for woody mature tendrils in the sun; anthocyanin is absent.

Growing tips (young shots):

*Pubescence*.—Absent.

*Color*.—RHS 144D.

*Anthocyanin*.—Absent.

*Shape*.—Similar to a shepherd's crook, that is, hook-shaped and naked on vigorously growing shoots.

*Apex*.—Exposed, leaves do not encompass the growing apex.

Leaves:

*Shape*.—Palmate/cordate.

*Apex*.—Pointed.

*Base*.—Sagittate.

*Margin*.—Dentate.

*Length of teeth on margin*.—⅛ inch to ⅜ inch.

*Shape of teeth on margin*.—Dentate.

*Texture, mature leave, upper and lower surfaces*.—Smooth.

*Size*.—Immature leaf, length: 1⅜ inch, blade only, $9^{th}$ leaf on a vigorous shoot. Immature leaf, width: 1½ inch, blade only, $9^{th}$ leaf on a vigorous shoot. Mature leaf, length: 3⅝ inch, mature blade only. Mature leaf, width: 4 inches, mature blade only.

*Color, immature leaf, both upper and lower surfaces*.—RHS 144A.

*Color, mature leaf*.—Upper surface: RHS N137C. Lower surface: RHS 138B.

*Venation*.—Pattern: Palmate. Color, upper surface: RHS 146A. Color, lower surface: RHS 146D.

*Petiolar sinus*.—U-shaped, open.

*Petiole*.—Length: 2¾ inch. Diameter: 1/16 inch. Color: RHS N144B on current season growth and RHS 144A in the late fall.

Floral cluster:

*General description and location*.—Opposite leaves at the node.

*Quantity of florets per cluster*.—50 to 75.

*Length*.—2¼ inch.

*Width*.—1⅜ inch.

*Peduncle length*.—⅝ inch to 1 inch.

*Inflorescences*.—Hermaphroditic.

*Quantity of inflorescences per shoot*.—Normally there are two inflorescences per shoot, however, rarely, sometimes there are three.

*Stamen form*.—Upright.

*Pistil*.—Length is ⅛ inch, diameter is 3/64 inch at its widest point at the ovary, and color is RHS 153A.

*Filament length and color*.—7/64 inch and RHS 196C.

*Anther*.—Elliptical shape, color dehisced is RHS 18B.

*Stamen*.—6 to 7 stamens per floret, the length is 4/32 inch to 5/32 inch; length of anther is 3/64 inch with undehisced color of RHS 10D and RHS 11C with dehisced color.

*Date of bloom*.—Earliest is June 7.

*Pollen amount*.—Abundant.

*Calyptra*.—Sheds normally.

*Calyptra color*.—RHS N144D just before shedding.

Fruit:

*Time of year of commercial harvest and shipment*.—Mid to late September.

*Cluster*.—General: No secondary bunches. Size: Medium. Length, without peduncle: 2½ inches. Width: 2½ inches. Density: Medium. Shape and weight of cluster: Globular and 56 g. Peduncle: Length: ½ inch to 1 inch. Diameter: 1/16 inch. Color: RHS 177B. Number of berries per cluster: 6 to 15.

Berry: Size: Medium. Shape: Spherical. Uniformity: Berries range from ¾ inch to 15/16 inch diameter, which is acceptable for the trade. Brix content: 16.0. Length: ¾ inch to 15/16 inch. Diameter: ¾ inch to 15/16 inch. Skin color: Berry skin color can range from RHS 153B to RHS 152C to RHS 199A to RHS N199A. Waxy bloom: Absent. Weight of individual berry: 5.4 g. Pedicel: Length: 3/16 inch. Diameter: 1/16 inch. Color: RHS N199B. Strength of attachment to berry: Moderate to strong; minimal shelling. Flesh: Color: Translucent, RHS 150D. Juice color: Clear. Juice production: Moderate to high. Thickness of skin: 1/16 inch. Flavor: Fruity, musky, typical of muscadine flavor. Fragrance: Very aromatic, typical of muscadine aroma. Texture: Mucilaginous/melting, where melting means the physical mass of the pulp reduces to a significant extent, releasing abundant juice.

Seeds: Stenospermocarpic seedless vine; seed remnant is less than 1/16 inch in length and not noticeable in consumption; main use is as fresh fruit, with possible use in processing for juice or wine.

Disease and insect resistance: Typical of *V. toundifolia*; no powdery mildew seen on vine or fruit, not entirely free of berry rot, which is usually minimal.

COMPARISON WITH PARENTAL AND COMMERCIAL VARIETIES

The female parent, 'JB94-38-7-44', differs from 'JB06-43-6-22' in that the female parent is seeded, while 'JB06-43-6-22' is stenospermocarpic.

The male parent, 'JB03-20-1-21' differs from 'JB06-43-6-22' in that the male parent has only slight muscadine aroma and flavor, while 'JB06-43-6-22' has typical pronounced muscadine aroma and flavor.

When 'JB06-43-6-22' is compared to the commercial variety 'Fry' (unpatented), 'JB06-43-6-22' is stenospermocarpic, has an average of 5.4 g per berry weight, and smaller berries that Fry, while 'Fry' is seeded, has an average of 9.2 g per berry weight and has larger berries than 'JB06-43-6-22'.

When 'JB06-43-6-22' is compared to its sibling 'JB06-43-6-21' (unpatented), 'JB06-43-6-22' has a more lyre-shaped petiolar sinus, is more resistant to fruit spoilage, and less cold hardy than 'JB06-43-6-21', while 'JB06-43-6-21' has a more obtuse-shaped petiolar sinus, is less resistant to fruit spoilage and rot than 'JB06-43-6-22', and is more cold hardy than 'JB06-43-6-22'.

I claim:

1. A new and distinct variety of grapevine plant designated 'JB06-43-6-22' as illustrated and described herein.

* * * * *